US005516504A

United States Patent [19]

Tomlinson

[11] Patent Number: 5,516,504

[45] Date of Patent: May 14, 1996

[54] CONCENTRATED WATER-FREE AEROSOL SPACE SPRAY

[75] Inventor: Roderick P. J. Tomlinson, Victoria, Australia

[73] Assignee: Soltec Research Pty. Ltd., Rowville, Australia

[21] Appl. No.: 983,520

[22] Filed: Mar. 3, 1993

[30] Foreign Application Priority Data

Sep. 3, 1990 [AU] Australia ................................ PK2089

[51] Int. Cl.$^6$ .................................................. A61K 9/12

[52] U.S. Cl. ............................ 424/45; 424/47; 424/76.1; 424/76.5; 424/405; 424/DIG. 10; 514/919; 128/200.23

[58] Field of Search .............................. 424/45, 47, 76.1, 424/76.5, 405, DIG. 10; 252/305, 306; 514/919; 128/200.23

[56] References Cited

U.S. PATENT DOCUMENTS

| | | | |
|---|---|---|---|
| 2,070,167 | 2/1937 | Iddings | 167/13 |
| 2,321,023 | 6/1943 | Goodhue et al. | 167/22 |
| 2,524,590 | 10/1950 | Boe | 252/305 |
| 3,756,472 | 9/1973 | Vos | 222/189 |
| 4,083,954 | 4/1978 | Tsuchiya et al. | 424/47 |
| 4,174,386 | 11/1979 | Spitzer et al. | 424/47 |
| 4,439,342 | 3/1984 | Albanese | 252/305 |
| 4,740,366 | 4/1988 | Winston et al. | 424/45 |
| 4,826,674 | 5/1989 | Albanese | 424/45 |
| 4,851,212 | 7/1989 | Winston et al. | 424/45 |

FOREIGN PATENT DOCUMENTS

| | | | |
|---|---|---|---|
| 512912 | 1/1977 | Australia . | |
| 58959/80 | 6/1980 | Australia . | |
| 594736 | 7/1987 | Australia . | |
| 1106329 | 4/1981 | Canada | 424/45 |
| 53-79928 | 7/1978 | Japan . | |
| 53-044494 | 11/1978 | Japan . | |
| 59-64688 | 4/1984 | Japan . | |
| 63-137981 | 6/1988 | Japan . | |
| 224382 | 1/1990 | Japan . | |
| 269407 | 3/1990 | Japan . | |
| 166861 | 12/1964 | U.S.S.R. . | |

*Primary Examiner*—Thurman K. Page
*Assistant Examiner*—Raj Bawa
*Attorney, Agent, or Firm*—Synnestvedt & Lechner

[57] ABSTRACT

A dispenser for space spraying an aerosol composition comprising a container for containing the aerosol composition and a metering device for space spraying a metered amount of he composition. The composition comprises active ingredient and propellant wherein the propellant is dissolved in the active ingredient. In preferred form, the composition comprises a non-aqueous solution containing 20–85% w/w active ingredient, 0–25% w/w co-solvent and 15–80% w/w propellant.

24 Claims, 1 Drawing Sheet

CONCENTRATED WATER-FREE AEROSOL SPACE SPRAY

BACKGROUND OF THE INVENTION

1. Field of the Invention

The invention relates to an aerosol space spray containing ultra high concentrations of active ingredients.

Throughout this specification the term "space spray" will be used to define aerosol formulations used for dispersion of an active ingredient in the air as opposed to aerosol formulations which are used to apply an active ingredient to a surface, e.g. antiperspirants, polishes, surface disinfectants etc.

2. Description of the Prior Art

Aerosol formulations have been known for at least 50 years in the art of aerial dispersion of insecticides, air fresheners and other active ingredients.

Conventionally, to obtain the desired characteristics of an aerosol for dispersion into the air or otherwise, the formulations contain minimal active ingredients, a solvent for the active ingredient and a suitable propellant. The active ingredient usually constitutes less than 1% w/w. The solvent is present in the order of 10–20% w/w and the propellant constitutes 80–90% w/w. In most cases of such aerosol formulations, the solvent is a hydrocarbon solvent and the propellant a fluorocarbon or hydrocarbon. Alternatively, the propellant is partially substituted with water, wherein the weight percentage being water is in the range of 30–40% w/w. Therefore it is evident that to deliver one gram of insecticide conventionally requires the release to the atmosphere of between 80 and 250 g of volatile organic compounds (VOC's). Volatile organic compound (VOC) is the general name given for compounds with an appreciable vapour pressure, for example, fluorocarbons, hydrocarbons i.e. kerosene, butane etc. commonly used as propellants.

In surface applications dispersal of the active ingredient of the aerosol over a large area is not vital to the efficacy of the formulation. In many surface sprays it is also important that the active ingredient contact the surface in high concentrations and often for a lengthy period of time - this is particularly important in the case of disinfectants. Accordingly, and in general, aerosol surface sprays containing high amounts of active ingredient are known.

CA 1106329 (BRISTOL-MYERS COMPANY) discloses an antiperspirant formulation comprising about 20–50% w/w of a solid antiperspirant material suspended in about 20–50% w/w of an appropriate oil. About 20–50% w/w of an appropriate propellant is also present in addition to a suspending agent and other adjuvants. In this formulation, the solid active ingredient is suspended in the oil which in turn is suspended throughout the propellant.

Another type of aerosol surface spray is disclosed in JP 78044494 ((TOKA-) TOKYO AEROSOL KAGAKU KAISHA) wherein 65–85 vol % of raw paint liquid, 35–15 vol % of a propellant and a solvent containing not less than 55 vol % (with respect to the paint) of acetone are combined together. The paint is solubilised by the solvent and in turn dissolved in the propellant.

An attempt to increase the amount of powdered solid active ingredient in an aerosol composition was described in AU 512912. In the formulation described at least 15% powdered solid active ingredient is dispersed in an emulsion of water and an anhydrous carrier. Added to this dispersion is then an anhydrous condensed hydrocarbon aerosol propellant gas miscible with the anhydrous carrier so that a final emulsion in which the active ingredient is dispersed is formed. It will be understood that, as in the prior art outlined hereinabove, the active ingredient in this formulation is dispersed or dissolved throughout the propellant. A stated result of this composition is that smaller amounts of propellant gas are required than is conventional for aerosols of this type.

AU 594736 (CHURCH & DWIGHT CO. INC.) discloses an air deodorizer comprising an aerosol having as the dispersed phase, liquid droplets comprising 2–25% of a deodorizing agent. Fragrance may also be included in the deodorizer in an amount of up to 3% by weight of the solution. A propellant in an amount of 8–40% by weight of the resulting aerosol spray may be present as a means for dispersion of the deodoriser.

In a formulation described in AU-B-58959/80 a novel hydrogenated hydrocarbon is described for use as a solvent in aerosol sprays. More particularly 10–89.5% of halogenated hydrocarbon as solvent is claimed in conjunction with 10–70% of liquified aerosol propellant and 0–75% of other organic solvents. Again it is clear that it is the function of the hydrocarbon and other solvents in this formulation to act as solvents of the active ingredient which is present in comparatively small amounts.

According to the prior art, especially in relation to insecticides, in order to solvate pyrethrins and synthetic pyrethroids and other insecticides sufficiently to provide break up energy to fully atomise the insecticide into fine atomised particle dispersions, it is clear that large amounts of propellant and solvents are required in proportion to the active ingredient.

It is apparent that with a general trend around the world for manufacturers and producers to be more environmentally aware as a result of, primarily, Government constraints and consumer demand, there is a real need to reduce the fluorocarbons, hydrocarbons and other VOC's released into the atmosphere since it is thought that they contribute significantly to atmospheric pollution.

Much research has been performed in search of finding a substitute propellant for the conventional fluorocarbon and hydrocarbon propellants for example, by the substitution of water for some of the hydrocarbons; however, a comparative substitute is yet to be found. By way of the water substitute example, water based aerosols do function to disperse the active ingredient but generally not in sufficiently fine enough drops for adequate air dispersal.

Accordingly it is an object of this invention to ameliorate at least some of the disadvantages of the prior art.

More particularly, it is an object of this invention to achieve an improved aerosol space spray which requires less release of undesirable VOC's into the environment. Most desirably, it is another object of the invention to substantially reduce the amount of VOC's required in an aerosol space spray.

SUMMARY OF THE INVENTION

To this end there is provided a dispenser for space spraying consisting of a container comprising a metering device, and a composition essentially comprising 20–85% w/w active ingredient in adjunct with suitable propellants, solvents and adjuvants.

Surprisingly, it has been found that by providing a stable ultra concentrated aerosol, the percentage of undesirable VOC's required as propellants and solvents is dramatically decreased, resulting in less VOC release into the atmosphere. As an added benefit, as a result of the decreased requirement for VOC's, the size of the container used for the aerosol in commercial applications is substantially reduced.

The aerosol arrangement of the invention can be used in essentially any system wherein the active ingredient is to be dispersed into the air or is atomised, for example, insecticides and air fresheners.

DESCRIPTION OF THE PREFERRED EMBODIMENTS

Figure 1:
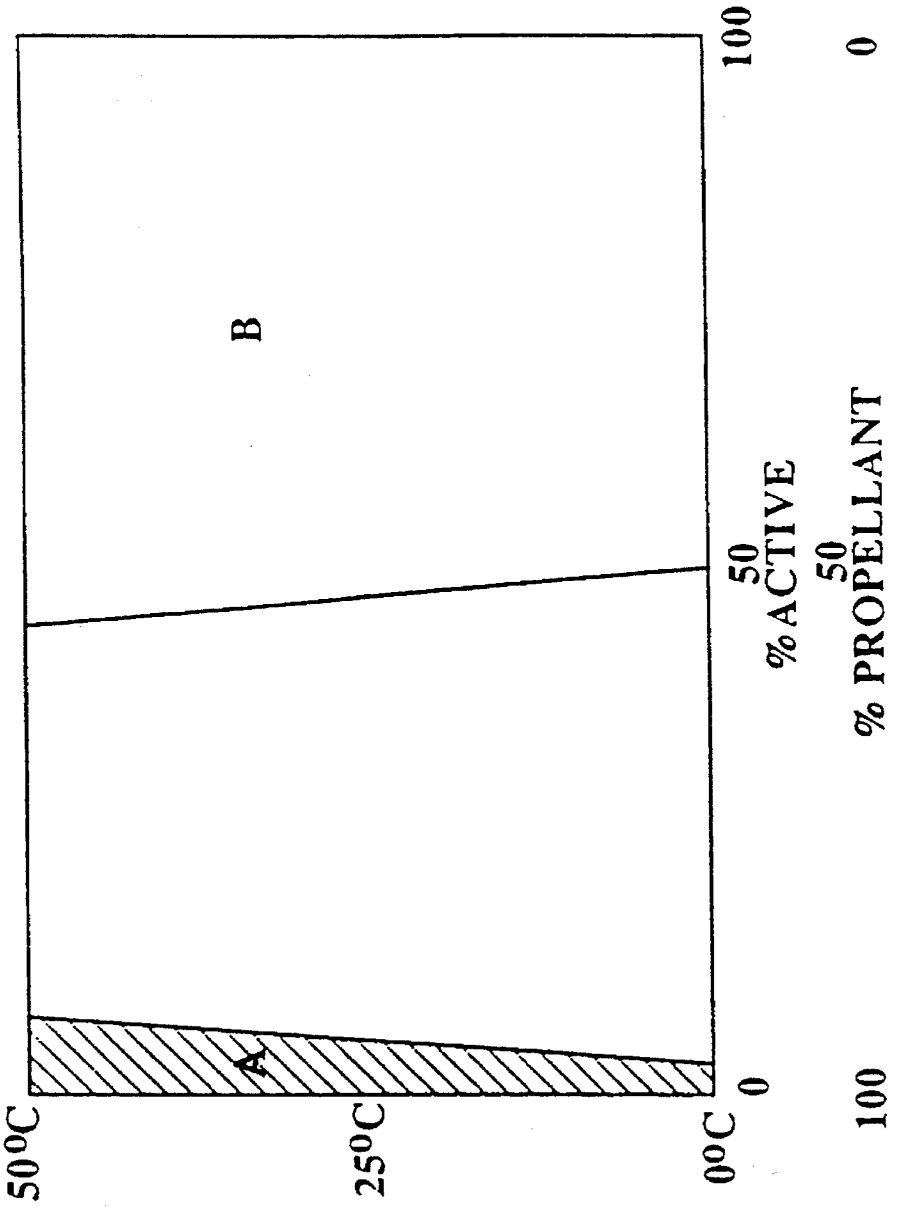
FIG. 1 is a phase diagram for ranges of concentration of active and propellant at various temperatures.

In some situations, a solvent may be required in the aerosol, but will generally be in the range of 0–25% w/w.

In the aerosol dispensers according to the invention, the active ingredients preferably act as solvents for the propellant and, as such, the propellant will accordingly be chosen to suit the active ingredients. This invention is partly predicated on the discovery that a small amount of propellant solvated in an insecticide, perfume or other active ingredient achieves effective space dispersion of the active ingredient.

In the case of insecticides, most normal household insecticides are suitable for use in the dispensers of the invention. For example, pyrethrins or synthetic pyrethroids may preferably be used although other conventional insecticides may be envisaged within the scope of the invention.

In the case of air fresheners, again, most conventional perfumes will be suitable for use. Throughout the specification, the term "perfume" refers to a substance which is pleasant-smelling and which is preferably in the form of a solution of natural and/or synthetic odor concentrates. The perfume can preferably be used in pure form and as a result thereof an added advantage is lent to such air fresheners inasmuch as the fragrance quality is unadulterated by the presence of high quantities of solvents and emulsifiers present in conventional systems.

Suitable propellants in accordance with the invention include fluorocarbons, hydrocarbons, dimethyl ether and any other propellants regarded as suitable, and in particular, suitable for household aerosols.

Although not essential to the dispensers of the invention, typical solvents which may be used include methylene chloride, 1,1,1-trichloroethane, ethanol, propanol; aromatic compounds such as toluene; glycol ethers such as carbitol; paraffin solvents such as hexane and petroleum solvent blends such as Shellsol T. However, as previously indicated, it is desirable to minimise and where possible obviate the need for these solvents.

In addition to the aforesaid ingredients, other auxiliary agents may be incorporated in the present composition for e.g. anticorrosive agents etc. and in the case of an insecticide, fragrance. Preferably, these adjuvants are present in a quantity of 1–10 % w/w. Suitable adjuvants may be perfumes, anti oxidants such as BHT, corrosion inhibitors such as cyclohexylaminenitrate.

Generally, it is envisaged that the aerosol will be used in a domestic situation and thus the aerosol container will meet the standard International pressure requirements.

It is realised that due to the higher concentration of active ingredient, there would possibly be a tendency to spray excess active ingredient into the atmosphere. To circumvent this problem an aerosol metered valve is preferably incorporated with the aerosol of the present invention. A typical dosage will be in the order of 5–500 mg. A more preferred dosage is in the order of 35–155 mg.

Preferably, because of the solvation characteristics of the active ingredients themselves, some specific polymers may be more desirably used as internal gaskets and metering devices in the dispensers of the invention than others. Such suitable polymers are preferably highly solvent resistant. Preferred metering valves for use in the invention may include a Valois DF10–150. Other possible valves may be supplied by COSTER, SEAQUIST or EMSON VALVES of the USA.

In another aspect of the invention there is provided a composition for use in a dispenser for space spraying essentially comprising 20–85% w/w active ingredient in adjunct with suitable propellants, solvents and other adjuvants.

Preferably, the composition comprises 20–85% w/w active ingredient and 80–15 % w/w propellant. If necessary, an additional solvent in an amount of 0–25% w/w may be present. Other adjuvants and excipients may also be present in an amount of 0–10 %.

Suitable active ingredients depending on the purpose of the space spray, propellants, solvents and excipients are outlined hereinabove in relation to the dispensers according to the invention.

In a further embodiment of the invention there is provided a composition for use in a dispenser for space spraying comprising at least one propellant fully solvated in at least one active ingredient.

Preferably, such a composition comprises 80–15% w/w of a propellant which is fully solvated in 20–85% w/w active ingredient.

Compositions according to this aspect of the invention may additionally comprise 0–25% w/w solvent, the solvent also being fully solvated in at least one active ingredient. Conveniently included are also 0–10% w/w of other suitable excipients or adjuvants.

Suitable active ingredients according to the application of the composition in accordance with this embodiment of the invention, suitable propellants, solvents and adjuvants are as described hereinabove in relation to the dispensers according to the invention.

In all aspects of this invention, the active ingredient in the defined range of the invention acts as the more continuous phase wherein the propellant is dispersed or dissolved to form an homogeneous phase.

Since a homogeneous phase is produced it is believed that the propellant is dissolved in the active ingredient.

FIG. 1 illustrates a phase diagram for concentrate technology wherein the differences between the different embodiments of this invention and the compositions of the prior art is illustrated.

On the FIG. A and B are single phase homogeneous solutions.

A is the zone of conventional aerosol formulation with low levels of actives dissolved in high levels of propellants, generally requiring added solvents.

B is the zone defining the new technology whereby the propellant is believed to be dissolved in the active to form homogeneous solutions. The region in between regions A and B is a two phase region unsuitable for use in aerosol formulations.

At 25° C. pyrethrin is soluble at less than 1% in hydrocarbon propellants and most perfumes at less than 5%. However as will be shown pyrethrins, synthetic pyrethroids and perfumes form an homogeneous solution across a broad range of concentrations of hydrocarbon propellant.

In the examples given herein below, the propellant solubility at 20° C. is measured by observation on a sliding scale wherein "clear" indicates complete solubility of the propellant in the active ingredient, "slight haze" indicates the first visible indications of insolubility whilst "turbid" indicates virtually complete insolubility.

HCP58 hydrocarbon is considered representative of all hydrocarbons available for use as propellants in compositions of the type exemplified hence its choice for the examples given hereinbelow.

In the case where the active ingredient is a perfume, the following examples illustrate the range of formulations possible within the scope of the invention.

In the experimental data given hereinbelow in which turbidity of the composition is measured, samples were packaged in glass aerosols in order that stability could be evaluated.

EXAMPLE A1

Perfume: 5286 GIVAUDIN

Propellant: HCP58 HYDROCARBON

| % w/w Perfume | % w/w Propellant | Propellant Solubility 20° C. |
|---|---|---|
| 100 | 0 | clear |
| 90 | 10 | clear |
| 80 | 20 | clear |
| 70 | 30 | clear |
| 61 | 39 | clear |
| 60 | 40 | slight haze |
| 59 | 41 | slight haze |
| 58 | 42 | slight haze |
| 55 | 45 | slight haze |
| 50 | 50 | haze |
| 40 | 60 | turbid |
| 30 | 70 | turbid |
| 20 | 80 | turbid |
| 10 | 90 | turbid |
| 0 | 100 | clear |

It is evident that a concentration in excess of 40% of propellant will result in separation and precipitation of insoluble perfume components. Such insoluble components will probably lead to valve failure in the dispenser and are therefore clearly undesirable.

Given that at least 15% w/w of propellant is required in the compositions according to the invention in order that sufficient expansive energy is provided to the active ingredient, it can be seen that an appropriate composition of this type might include 61–85% w/w perfume and 39–15% w/w propellant.

These weight ranges can be compared with prior art aerosol fragrances wherein levels above approximately 0.5% of fragrances are not used due to the insolubility of the fragrance in the propellant.

EXAMPLE A2

Perfume: NOUVELLE 301

Propellant: HCP58 HYDROCARBON

-continued

| % w/w Perfume | % w/w Propellant | Propellant Solubility 20° C. |
|---|---|---|
| 100 | 0 | clear |
| 90 | 10 | clear |
| 80 | 20 | clear |
| 70 | 30 | clear |
| 65 | 35 | clear |
| 60 | 40 | clear |
| 59 | 41 | clear |
| 58 | 42 | slightly turbid |
| 55 | 45 | turbid |
| 50 | 50 | turbid |
| 40 | 60 | turbid |
| 30 | 70 | turbid |
| 20 | 80 | turbid |
| 10 | 90 | turbid |
| 0 | 100 | clear |

Again, it is evident that a composition-comprised of 58–85% w/w perfume and 42–15% w/w propellant will be homogenous and thus suitable for use.

EXAMPLE A3

In this example the effect of the addition of a solvent upon the compositions according to the invention was tested.

Perfume: NOUVELLE 301

Propellant: HCP58 HYDROCARBON

| % w/w Perfume | % w/w Propellant | % w/w Solvent | Solubility at 20° C. |
|---|---|---|---|
| 20 | 65 | 15 | slightly turbid |
| 20 | 62 | 18 | slightly turbid |
| 20 | 61 | 19 | slightly turbid |
| 20 | 60 | 20 | clear |
| 20 | 55 | 25 | clear |
| 40 | 55 | 5 | slightly turbid |
| 40 | 53 | 7 | slightly turbid |
| 40 | 52 | 8 | slightly turbid |
| 40 | 51 | 9 | clear |
| 40 | 50 | 10 | clear |

Clearly, the active ingredient, perfume, is an effective substitute for solvents in the compositions of the invention; the higher the level of perfume (40% w/w) the less solvent is required in order to form a single phase homogenous liquid. Conventionally the active ingredient: propellant: solvent ratio is approximately 1:85:15 whereas in this instance the solution is quite clearly an homogenous solution in the ratio of approximately 1:1.25:0.25. It is evident that whereas in the prior art compositions in order to increase the perfume level, the undesirable solvent levels were increased, in fact surprisingly quite the opposite has been found to be true.

In the case where the active ingredient is an insecticide, the following examples illustrate the range of formulations possible within the scope of the invention.

These results can be compared to a prior art household insecticide formulation which conventionally comprises:

Pyrethrins (active) 0.3% w/w

Piperonyl Butoxide (pyrethroid synergist) 1.5% w/w

ShellSolT (solvent) 15.0% w/w

Trichloroethane (solvent) 25.2% w/w

HLP58 Hydrocarbon (propellant) 58.0% w/w i.e. the active ingredient: propellant: solvent ratio is approximately 1:22:32.

In each of the examples given hereinbelow the formulations were prepared in glass aerosols and their clarity examined after 24 hours.

EXAMPLE B1

Insecticide: 50% KENYA PYRETHRUM EXTRACT

Synergist: 85% PIPERONYL BUTOXIDE (The insecticide and the synergist were combined in a ratio of 1:4)

Propellant: HCP58 HYDROCARBON

| % w/w Insecticide | % w/w Propellant | Solubility 20° C. |
|---|---|---|
| 100 | 0 | clear |
| 90 | 10 | clear |
| 80 | 20 | clear |
| 70 | 30 | clear |
| 60 | 40 | clear |
| 50 | 50 | clear |
| 40 | 60 | clear |
| 39 | 61 | slight haze |
| 38 | 62 | slight haze |
| 37 | 63 | slight haze |
| 35 | 65 | slight haze |
| 30 | 70 | slight haze |
| 20 | 80 | turbid |
| 10 | 90 | turbid |
| 0 | 100 | clear |

Again, on the understanding that at least 15% w/w propellant is required in order that sufficient expansion energy is provided to the active ingredient, it can be seen that a composition suitable for use can be comprised of 40–85% w/w insecticide and 60–15% w/w propellant.

EXAMPLE B2

Insecticide: SUMETHRIN

Propellant: HCP58 HYDROCARBON

| % w/w Insecticide | % w/w Propellant | Solubility 20° C. |
|---|---|---|
| 100 | 0 | clear |
| 90 | 10 | clear |
| 80 | 20 | clear |
| 79 | 21 | slight haze |
| 78 | 22 | slight haze |
| 76 | 24 | smoky |
| 70 | 30 | smoky |
| 60 | 40 | smoky |
| 50 | 50 | smoky |
| 40 | 60 | turbid |
| 30 | 70 | turbid |
| 20 | 80 | turbid |
| 10 | 90 | turbid |
| 0 | 100 | clear |

It can be seen that suitable compositions might comprise 80–85% w/w insecticide and 20–15% w/w propellant.

In order to test the effect of the presence of a solvent on this composition, 5% w/w solvent was added to the composition. This amount of solvent enabled a solution of 50% w/w insecticide and 45% w/w propellant which was completely clear and thus suitable for use.

EXAMPLE B3

Insecticide: BIORESMETHRIN/BIOALLETHRIN 1:5

Propellant: HCP HYDROCARBON 58

| % w/w Insecticide | % w/w Propellant | Solubility 20° C. |
|---|---|---|
| 100 | 0 | clear |
| 90 | 10 | clear |

-continued

| % w/w Insecticide | % w/w Propellant | Solubility 20° C. |
|---|---|---|
| 80 | 20 | clear |
| 70 | 30 | clear |
| 68 | 32 | clear |
| 66 | 34 | clear |
| 64 | 36 | clear |
| 63 | 37 | slightly turbid |
| 62 | 38 | slightly turbid |
| 60 | 40 | turbid |
| 50 | 50 | turbid |
| 40 | 60 | turbid |
| 30 | 70 | turbid |
| 20 | 80 | turbid |
| 10 | 90 | turbid |
| 0 | 100 | clear |

Satisfactory atomisation of the insecticide is achieved in compositions having 64–85 w/w insecticide and 36–15% w/w propellant.

Addition of 5% w/w solvent enabled a higher quantity of propellant to be dissolved in the insecticide.

EXAMPLE C1

In order to test the efficacy of the compositions according to the invention, the composition described in Example B1 in a ratio of 50% w/w insecticide blend to 50% w/w propellant was packaged in a 10 mg aluminium aerosol and fitted with a 150 mg metering valve.

PRODUCTS

1. Formulation—Aerosol Insecticide of Example B1

Methods

For these tests, 5 replicates only were carried out for the Example B1 formulation using the CERIT Modified Hunting Mode protocol—'CERIT/HF-HM/FIK 2.0'—modified for manual operation and to allow the aerosol plume of the formulation to envelop the fly release cage fully.

MODIFIED HUNTING MODE PROTOCOL—AEROSOL CHAMBER TESTS-CERIT/HF-HM/FIK 2.0

Hunting Mode

Insects released to fly through the spray cloud, to simulate field use where the operator "aims at" the target(s), i.e. the "Hunting" method.

Order of Testing

The order of testing of formulations was chosen on a randomized block basis. Each formulation, including controls, was tested in each block; each block being completed on one day.

Five replicates of each test.

Controls

One run in each replicate block, without aerosol spray.

Insects

Houseflies—Musca domestica

Strain—"SYD 90", field collected 1990, from Sydney, various areas.

Resistance status—susceptible (equivalent to SYD 88).

Pre-fed sugar only, no protein.

Age at time of test—3 to 7 days.

Sex—mixed.

Transferred directly from cage to release container without anaesthesia.

Numbers used per test—approx. 50.

Sprays

Formulation—supplied as a very small aerosol.

Spray rate—pre-calibration of aerosol before use; aerosol shaken (inverted) immediately before spraying.

Spray start—at time zero.

Spray duration—manually.

Weight sprayed—0.08 g.

Insect Release

Released into chamber—mechanically, under computer control, 0.8 m in front of, and 20 cm above, nozzle.

Time of release—2 s.

K.D. Counts

Counting—visually.

Times of Counts (From Time Zero), in Seconds:

30, 60, 90, 120, 150, 180, 240, 360, 480, 720.

Evacuation of Aerosol

Vents opened and exhaust fan on for 15 mins after each test.

Recording

Computer, disk and printout.

Preliminary Analyses

Log dose/probit analysis—a modified program.

$KDT_{50}$ s and 95% confidence limits are determined.

Data then subjected to analysis of variance program and Student-Newman Keuls test.

Mortality

Insects held in containers provided with sugar and water for 24 h counts of mortality.

The modifications to this protocol for the purposes of this example were as follows:

1. a reduction in spraying distance from 1.8 m to 0.8 m because of the low plume projection or 'throw' of the formulation;
2. a reduction in the standard 2 g delivery of insecticide to a metered dose delivery of approximately 0.08 g;
3. and manual actuation of the formulation instead of computer-controlled actuation.

Analyses

The times for 50% of the insects to be knocked down ($KDT_{50}$ s) were calculated by probit analysis (Finney, D.J., 1971. Probit Analysis. 3rd ed. Cambridge Univ. Press, London. 333 pp). Analysis of variance (ANOVA—Sokal and Rohlf "Biometry", Freeman, 1981) was applied to the $KDT_{50}$ s for all formulations.

TABLE 1

$KDT_{50}$s (sec) and the 24 h mortalities (%) for Modified Hunting Mode, 1 metered dose per run = 0.08 g spray, 2 sec release.

| Formulation | Mean $KDT_{50}$ (sec) | 95% C-Limits (sec) | Mean Mortality (%) |
|---|---|---|---|
| Supersol | 116 | 108–124 | 100 |

In the tests for Modified Hunting Mode, the formulation of Example B1 was effective in the knockdown and kill of Musca domestica, where a $KDT_{50}$ of 116 seconds and 100% mortality was achieved (from Table 1 ).

Based on the efficacies of formulations that are available on the market, the results for the formulation of Example B1 are comparable with mid-range products, i.e. total knockdown and mortality (100%) is achieved within 2 minutes of spraying.

It is apparent from the examples given hereinabove that whereas in conventional household aerosols, solvent/insecticide ratios can be as high as 100:1 and propellant ratios even higher, in the formulations of the instant invention, the solvent/insecticide ratio is less than 1:5 and often zero and the propellant ratios less than 1:1.

It is also therefore apparent that in accordance with these embodiments wherein the active ingredient is either an insecticide or a perfume, the delivery of one gram of active component is accompanied by the release of only one gram of VOC's, or indeed less. This represents a 100 fold reduction in VOC release in comparison to prior art formulations.

It is to be understood that the preceding examples are intended to illustrate but not limit the compositions and dispensers of the instant invention. It will be understood that the scope of the invention may include such active ingredients as anti-microbial agents and may be extended to include other solvents, adjuvants and propellants not specifically illustrated.

I claim:

1. A water-free aerosol composition consisting essentially of a solution of about 20 to about 85% w/w of a livid active ingredient selected from the group consisting of pyrethrin insecticides, pyrethroid insecticides, perfumes and mixtures thereof, and about 15 to about 80% w/w of a propellant selected from the group consisting of hydrocarbons, fluorocarbons and dimethyl ether, said propellant being dissolved in said active ingredient.

2. The composition according to claim 1 including also up to about 25% w/w of a co-solvent selected from the group consisting of methylene chloride 1,1,1-trichloroethane, lower alkanols, aromatic solvents, glycol ethers, paraffin solvents and petroleum solvents, said propellant being dissolved in said co-solvent and said active ingredient.

3. The composition according to claim 1 or 2 wherein said active ingredient is perfume.

4. The composition according to claim 1 or 2 wherein said active ingredient is selected from the pyrethrin and pyrethroid insecticides.

5. The composition according to claim 3 which consists essentially of about 55 to about 85% w/w of said perfume and about 15 to about 45% w/w of said propellant.

6. The composition according to claim 3 which consists essentially of about 20 to about 40% w/w of said perfume, about 5 to about 25% w/w of said co-solvent and about 50 to about 65% w/w of said propellant.

7. The composition according to claim 3 which consists essentially of about 40% w/w of said perfume, about 5% w/w of said co-solvent and about 55% w/w of said propellant.

8. The composition according to claim 4 which consists essentially of about 40 to about 85% w/w of said insecticide and about 15 to about 60% w/w of said propellant.

9. The composition according to claim 4 which consists essentially of about 65 to about 85% w/w of said insecticide, and about 15 to about 35% w/w of said propellant.

10. The composition according to claim 4 which consists essentially of about 50% w/w of said insecticide, about 5% w/w of said co-solvent and about 45% w/w of said propellant.

11. In a dispenser for space spraying an aerosol composition consisting essentially of:

(A) a container;

(B) an aerosol composition disposed within said container; and (C) a metering device operatively connected to said container for space spraying a metered amount of said aerosol composition, the improvement wherein said aerosol composition is a water-free aerosol composition consists essentially of a solution of about 20 to about 85% w/w of a liquid active ingredient selected from the group consisting of pyrethrin insecticides pyrethroid insecticides, perfumes and mixtures thereof, and about 15 to about 80% w/w of a propellant selected from the group consisting of hydrocarbons, fluorocarbons and dimethyl ether, said propellant being dissolved in said active ingredient.

12. The dispenser according to claim 11 wherein said composition additionally includes up to about 25% w/w of a co-solvent selected from the group consisting of methylene chloride, 1,1,1-trichlorethane, lower alkanols, aromatic solvents, glycol ethers, paraffin solvents and petroleum solvents, said propellant being dissolved in said co-solvent and said active ingredient.

13. The dispenser according to claim 11 or 12 wherein said active ingredient is perfume.

14. The dispenser according to claim 11 or 12 wherein said active ingredient is selected from the pyrethrin and pyrethroid insecticides.

15. The dispenser according to claim 13 in which the composition consists essentially of about 55 to about 85% w/w of said perfume and about 15 to about 45% w/w of said propellant.

16. The dispenser according to claim 13 in which the composition consists essentially of about 20 to about 40% w/w of said perfume, about 5 to about 25% w/w of said co-solvent and about 50 to about 65% w/w of said propellant.

17. The dispenser according to claim 13 in which the composition consists essentially of about 40% w/w of said perfume, about 5% w/w of said co-solvent and about 55% w/w of said propellant.

18. The dispenser according to claim 14 in which the composition consists essentially of about 55 to about 85% w/w of said insecticide and about 15 to about 45% w/w of said propellant.

19. The dispenser according to claim 14 in which the composition consists essentially of about 20 to about 40% w/w of said insecticide, about 5 to about 25% w/w of said co-solvent and about 50 to about 65% w/w of said propellant.

20. The dispenser according to claim 14 in which the composition consists essentially of about 40% w/w of said insecticide, about 5% w/w of said co-solvent and about 55% w/w of said propellant.

21. The composition according to claim 2, wherein said co-solvent is selected from the group consisting of methylene chloride, 1,1,1-trichloroethane, ethanol, propanol, toluene, carbitol and hexane.

22. The dispenser according to claim 12, wherein said co-solvent is selected from the group consisting of methylene chloride, 1,1,1-trichloroethane, ethanol, propanol, toluene, carbitol and hexane.

23. The composition according to claim 4, wherein said pyrethroid insecticide is a synthetic pyrethroid.

24. The dispenser according to claim 14 wherein said pyrethroid insecticide is a synthetic pyrethroid.

* * * * *

UNITED STATES PATENT AND TRADEMARK OFFICE
CERTIFICATE OF CORRECTION

PATENT NO. : 5,516,504
DATED : May 14, 1996
INVENTOR(S) : Roderick P. J. Tomlinson It is certified that error appears in the above-identified patent and that said Letters Patent is hereby corrected as shown below:

Column 10, line 1, before the heading "TABLE 1", insert the heading --Results--.

Claim 1, Column 10, line 41, change "livid" to --liquid--.

Claim 2, Column 10, line 50, after "chloride", insert --,--.

Claim 11, Column 11, line 22, after "composition", insert --that--.

Claim 11, Column 11, line 25, after the first occurence of "insecticide", insert --,--.

Signed and Sealed this

Thirtieth Day of November, 1999

Attest:

Q. TODD DICKINSON

Attesting Officer

*Acting Commissioner of Patents and Trademarks*